(12) United States Patent
Sengupta et al.

(10) Patent No.: US 10,750,842 B2
(45) Date of Patent: Aug. 25, 2020

(54) BOTTLE

(71) Applicant: Soumalya Sengupta, Kolkata (IN)

(72) Inventors: Soumalya Sengupta, Kolkata (IN); Sanandan Sudhir, Ahmedabad (IN)

(73) Assignee: Soumalya Sengupta, Kolkata (IN)

( * ) Notice: Subject to any disclaimer, the term of this patent is extended or adjusted under 35 U.S.C. 154(b) by 2 days.

(21) Appl. No.: 16/093,146

(22) PCT Filed: Apr. 12, 2017

(86) PCT No.: PCT/IB2017/052104
§ 371 (c)(1),
(2) Date: Oct. 12, 2018

(87) PCT Pub. No.: WO2017/178980
PCT Pub. Date: Oct. 19, 2017

(65) Prior Publication Data
US 2019/0125063 A1 May 2, 2019

(30) Foreign Application Priority Data

Apr. 15, 2016 (IN) .............................. 201631013235
Jul. 19, 2016 (IN) .............................. 201631024755

(51) Int. Cl.
*G08B 21/22* (2006.01)
*A45F 3/16* (2006.01)
(Continued)

(52) U.S. Cl.
CPC ............ *A45F 3/16* (2013.01); *A47G 19/2227* (2013.01); *A47G 23/16* (2013.01); *A61B 5/00* (2013.01);
(Continued)

(58) Field of Classification Search
CPC .......... A24F 15/12; A24F 15/14; A24F 15/18; A24F 47/008; A61M 2209/045;
(Continued)

(56) References Cited

U.S. PATENT DOCUMENTS 10,329,061 B2 * 6/2019 Dias ..................... A47G 19/025
2003/0106907 A1 * 6/2003 Harrison ............... B05B 9/0861
222/383.1

(Continued)

FOREIGN PATENT DOCUMENTS

GB        2 370 561      * 12/2000

*Primary Examiner* — Daniel Previl
(74) *Attorney, Agent, or Firm* — Myers Bigel, P.A.

(57) ABSTRACT

The present disclosure relate to a smart and intelligent water bottle that can inform its user of his hydration needs by tracking water consumed by the user and also functions as a safety device by enabling user to transmit a SoS and GPS co-ordinates to predefined list of friends, family or official institutions. The bottle, while tracking water consumption, can differentiate between actual consumption and intended or unintended discharge of its contents. The bottle incorporates a panic button configured to recognize a genuine pressing of the panic button based on natural increase in heart rate of the user in case of emergencies. The disclosed bottle incorporates a capacitive sensor and a tilt sensor for measurement of water present in the bottle is done. In an aspect, the capacitive sensor is configured centrally within a hollow space in the bottle to prevent its contact with water.

20 Claims, 17 Drawing Sheets

(51) Int. Cl.
  *A61B 5/00* (2006.01)
  *A61B 5/0245* (2006.01)
  *A47G 19/22* (2006.01)
  *A47G 23/16* (2006.01)
  *A61B 5/024* (2006.01)
  *A45F 3/00* (2006.01)

(52) U.S. Cl.
  CPC ........ *A61B 5/0245* (2013.01); *A61B 5/02438* (2013.01); *A61B 5/6887* (2013.01); *A45F 2003/003* (2013.01); *A47G 2019/225* (2013.01); *A61B 2503/10* (2013.01)

(58) Field of Classification Search
  CPC ........ A61M 1/00; A61M 1/0005; A61M 1/02; A61M 5/007; A61M 5/1689; A61M 5/178; B65B 3/04; B65D 25/005; G01F 23/00; G01F 23/292; G09F 2023/0025; H02J 50/10; H02J 7/0042; H02J 7/0044; H02J 7/0052; H02J 7/0063; H02J 7/025; H02J 7/335; H05K 999/00; H05K 999/99; C08L 2666/02; C08L 23/02; C08L 51/006; C08L 51/06; C08L 53/00; C08L 23/20; C08L 2666/24; C08L 67/03; C08K 3/013; A45F 2003/003; A45F 3/16; A47G 19/2227; A47G 2019/225; A47G 23/16; A47J 27/2105; A61B 2503/10; A61B 2562/0214; A61B 5/00; A61B 5/02438; A61B 5/0245; A61B 5/1178; A61B 5/682; A61B 5/6887; A61J 7/0053; A61J 11/00; A61J 15/0011; A61J 15/0076; A61J 15/0084; A61J 2200/42; A61J 2200/72; A61J 2205/10; A61J 9/00; B01D 1/0023; B01F 15/06; B05B 11/0002; B05B 11/3057; B67D 3/0022; B67D 1/0041; B67D 1/1247; C01B 3/042; C01B 3/06; C02F 1/048; C02F 1/22; C02F 1/30; C02F 2103/08; C02F 1/325; C02F 2201/004; C02F 2201/005; C02F 2201/008; C02F 2201/009; C02F 2201/3228; C02F 2201/326; C02F 2303/04; C02F 2307/04; C02F 2307/10; C08F 10/14; C08F 110/14; C08F 210/14; C08F 255/00; C08F 255/02; C08F 293/00; C08F 293/005; F25C 1/12; F25C 2700/04; G06K 9/00885; G07F 13/02; G07F 13/10; G16H 20/13; Y02A 20/128; Y02A 20/211; Y02A 20/212; Y02E 60/364; Y02E 60/13; A23L 33/30; A45D 2200/056; A45D 2200/155; A45D 34/00; A47K 17/00; A61L 2202/14; A61L 2202/15; A61L 2209/11; A61L 2209/134; A61L 2/18; A61L 9/127; B01J 19/0046; B01J 2219/00286; B01J 2219/00391; B01J 2219/00416; B01J 2219/00423; B01J 2219/00488; B01J 2219/0059; B01J 2219/00596; B01J 2219/00686; B01J 2219/00725; B05C 17/002; B05C 17/0316; B07C 5/3404; B29B 11/04; B29B 11/14; B29B 2911/14053; B29B 2911/14066; B29B 2911/1408; B29B 2911/14093; B29B 2911/14146; B29B 2911/14306; B29C 45/1646; B29C 49/06; B29C 65/0672; B29C 65/606; B29C 66/1222; B29C 66/1226; B29C 66/126; B29C 66/1312; B29C 66/545; B29D 22/003; B29L 2009/001; C07K 1/045; C08G 63/605; C08J 2367/03; C08J 2427/00; C08J 5/18; C08J 7/047; C09J 151/006; C09J 151/06; C09J 153/00; C25D 1/08; C25D 3/66; C25D 5/56; C25D 7/00; C40B 40/10; C40B 60/14; E03D 9/005; F04B 17/046; F04B 49/12; F25B 2600/0251; G01N 2030/642; G01N 2033/0081; G01N 21/72; G01N 21/9027; G01N 30/74; G01N 30/78; G03D 3/06; G03D 7/00; G03G 15/0849; G03G 15/105; G09B 23/285; G09B 23/303; H01G 11/68; H01G 11/70; H01M 4/661; H01M 4/80; H04R 25/658; Y10S 128/03; Y10S 128/13; Y10T 137/2509; Y10T 137/469; Y10T 137/7303; Y10T 29/49826; Y10T 428/3154; Y10T 428/31786

USPC ........... 340/573.1, 531, 539.12, 539.32, 546, 340/568.1, 602, 636.18, 691.3, 825.49

See application file for complete search history.

(56) References Cited

U.S. PATENT DOCUMENTS

| | | | |
|---|---|---|---|
| 2004/0088345 A1* | 5/2004 | Zellner | G08B 25/006 709/200 |
| 2016/0025545 A1* | 1/2016 | Saltzgiver | G01F 23/263 73/304 C |
| 2019/0274456 A1* | 9/2019 | Hambrock | G01F 23/2921 |

* cited by examiner

BOTTLE

This is a Cognate Application titled "BOTTLE", taking priority from two provisional Applications 201631013235 filed on 15 Apr. 2016 & 201631024755 filed on 19 Jul. 2016.

TECHNICAL FIELD

The present disclosure relates to the field of fluid containers. In particular the present disclosure pertains to a smart water bottle that can inform its user of his hydration needs and also work as a safety device.

BACKGROUND

Background description includes information that may be useful in understanding the present invention. It is not an admission that any of the information provided herein is prior art or relevant to the presently claimed invention, or that any publication specifically or implicitly referenced is prior art.

It is usual for people to carry a water bottle to meet their water needs and keep their bodies well hydrated while travelling or doing other activities such as sports and athletic activities; and as also by many other like school children, office goers, patients to name a few. As primary function is to keep body well hydrated efforts have been made in the art to provide water bottle that includes functionality of informing a user of his hydration needs based on quantum of water consumed by him.

For example prior art reference WO 2013181455 A1 discloses a fluid bottle with flow meter attached through a straw or pour mouth piece of the bottle to enable measurement of the flow while consuming water through straw or by tilting. The flow meter measures the amount of fluid and/or the amount of an additive consumed by user which is displayed on a device. The disclosed bottle suffers from drawback that it cannot differentiate between consumption of the fluid/water by user and intended or unintended discharge of the fluid from the bottle.

It would therefore be desirable to have a water bottle that can differentiate between actual consumption and intended or unintended discharge of the fluid/water from the bottle. Besides above, being an inseparable companion of travelers and sportsmen, and many others, it would be useful if the water bottle can incorporate other desirable functionalities. These additional functionalities can also help in keeping other stakeholders such as parents, coaches, doctors, dieticians and caregivers informed of liquid intake by the user.

There is, therefore, a need in the art for a smart or intelligent water bottle that can differentiate between actual consumption of its content and intended or unintended discharge of the fluid/water from the bottle; and incorporate other desirable functionalities.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

OBJECTS OF THE INVENTION

A general object of the present disclosure is to provide a smart and intelligent water bottle that can inform its user if his hydration needs are met or not.

An object of the present disclosure is to provide a water bottle that, besides overcoming drawbacks of the known smart bottles, incorporates other desired functionalities.

An object of the present disclosure is to provide a water bottle with a capacitive sensor placed in a centrally located hollow space within the bottle to measure water level so that the sensor makes a more accurate measure of the water level and also does not come in contact with water.

Another object of the present disclosure is to provide a water bottle that makes an accurate assessment of its water content by using tilt of the bottle in addition to water level measurement.

Another object of the present disclosure is to provide a water bottle that can differentiate between actual consumption and intended or unintended discharge of its contents.

Another object of the present disclosure is to provide a user safety device in form of a water bottle by providing a panic button for use by its user in case of an emergency Another object of the present disclosure is to provide a water bottle that can send SOS and GPS co-ordinates to predefined list of friends, family or official institutions.

Yet another object of the present disclosure is to provide a water bottle that can recognize a genuine pressing of the panic button.

Still another object of the present disclosure is to provide a water bottle that can recognize a genuine pressing of the panic button based on heart rate of user.

SUMMARY

Aspects of the present disclosure relate to a smart and intelligent water bottle that can inform its user of his hydration needs by tracking water consumed by the user. In an aspect, the bottle, while tracking water consumption by its user, can differentiate between actual consumption and intended or unintended discharge of its contents.

In an aspect, the disclosed bottle incorporates a capacitive sensor for water level measurement based on which amount of water present in the bottle and therefore amount of water consumed is calculated. In another aspect, the capacitive sensor is configured internally within a centrally located hollow space in the bottle to enable it to provide a more accurate water level reading irrespective of tilt of the bottle. Placing the sensor within a hollow space prevents it from coming in contact with water.

In an aspect, an accurate assessment of water consumption is made by providing a tilt sensor, wherein the tilt sensor can give orientation of the bottle and the reading from the capacitive sensor can be interpreted taking into account the orientation/tilt of the bottle to arrive at an accurate assessment of water quantity in the bottle. In an aspect, tilt sensing can be performed based on acceleration data received from one or more accelerometers that are configured in/with the bottle, wherein the one or more accelerometers can provide speed and duration data that can help in computing the orientation of the bottle. In an aspect, speed and duration data provided by the accelerometers and the computed tilt angle can also be used to sense if person was drinking water. There can additionally be one or more proximity sensor at mouth or spout of the bottle, and signal from the proximity sensor coupled with data from the accelerometers can be used for an accurate sensing to differentiate between actual consumption by a person and intended or unintended discharge of its contents.

In an aspect, the disclosed water bottle can besides communicating its user of his hydration needs, can also work as a safety device. In an aspect, the disclosed water bottle can incorporate a panic button for use by user in case of emergency on which the bottle can transmit a SoS and GPS co-ordinates to predefined list of friends, family or official institutions.

In an embodiment, the panic button can be configured to prevent its accidental pressing and avoid false SoS. For this purpose, the panic button can be concealed behind a hatch or a sliding part or can incorporate a 2-3 step mechanism for actuation to prevent accidental pressing.

In an aspect, the panic button can be configured to recognize a genuine pressing of the panic button and transmit a SoS and GPS co-ordinates after ascertaining genuineness of the emergency, wherein determination of the genuineness of the emergency can be based on natural increase in heart rate of the user in case of emergencies. Accordingly, pressing of the panic button can result in transmission of SoS and GPS co-ordinates to predefined list of friends, family or official institutions only if detected heart rate of the user exceeds a pre-fined heart rate.

In an embodiment, in order to facilitate easy and fast ascertaining of genuineness of emergency, the panic button can incorporate a heart rate sensor such that touching of the panic button by the user can result in sensing of heart rate. The button can be configured for a sliding motion to activate panic button functionality. Combining the heart rate sensor with the panic button and need to slide the button to meet panic button functionality can also prevent accidental pressing of the panic button.

In an embodiment, the heart rate sensor configured on the panic button can, besides helping to ascertain genuineness of the actuation of the panic button, work as means to detect heart rate of the user such as patients, sportsmen etc.

In an embodiment, the panic button can be configured to override requirement of the sensed heart rate being more than the set threshold for sending the SoS and GPS co-ordinates. This can be implemented, for example, by providing a second sliding of the button in a direction different from the first sliding action such as in perpendicular direction.

In an embodiment, the disclosed bottle can be in Bluetooth connectivity with other computing devices such as a mobile phone/laptop/tablet PC, and transfer hydration data to an application installed in the computing device. In another embodiment, the computing device can incorporate a GSM module for wireless communication and the application can receive an indication of activation of the panic button over Bluetooth and enable transmission of the SoS and GPS co-ordinates through the GSM module of the computing device.

In an alternate embodiment, the disclosed water bottle itself can incorporate a GPS and GSM module to enable transmission of the SoS and GPS co-ordinates when the panic button is activated. A bottle that incorporate a GPS and GSM module to enable transmitting the SoS and GPS co-ordinates can meet requirement of those who may not be carrying a computing device with them such as school going children or sportsmen while engaged in sporting activity to name a few.

In an embodiment, the disclosed bottle can incorporate a touch screen for user interface. The screen can be configured at lid of the mouth of the bottle or at side cylindrical surface or at a handle among various options. The bottle can also incorporate a temperature sensor configured to sense body temperature of user. The temperature sensor can be positioned at side cylindrical surface or at handle among various options.

In an embodiment, the bottle can incorporate a processor configured to process and analyze data sensed by different sensors and signals received from buttons and compute various parameters such as tilt angle, orientation and posture of the bottle, amount of water in the bottle and accordingly water consumed by user, and thereafter issue warning/reminders to the user of his hydration need based on display in the screen or by buzzer or by warning lamps. The processor can further enable Bluetooth and/or GSM connectivity as the case may be.

In an embodiment, the GPS, processor and power storage means to power the processor and other accessories/devices can be housed at bottom of the bottle within a bottom cover or in a handle that can also incorporate panic button and temperature sensor.

Various objects, features, aspects and advantages of the inventive subject matter will become more apparent from the following detailed description of preferred embodiments, along with the accompanying drawing figures in which like numerals represent like components

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION

Figure 1:
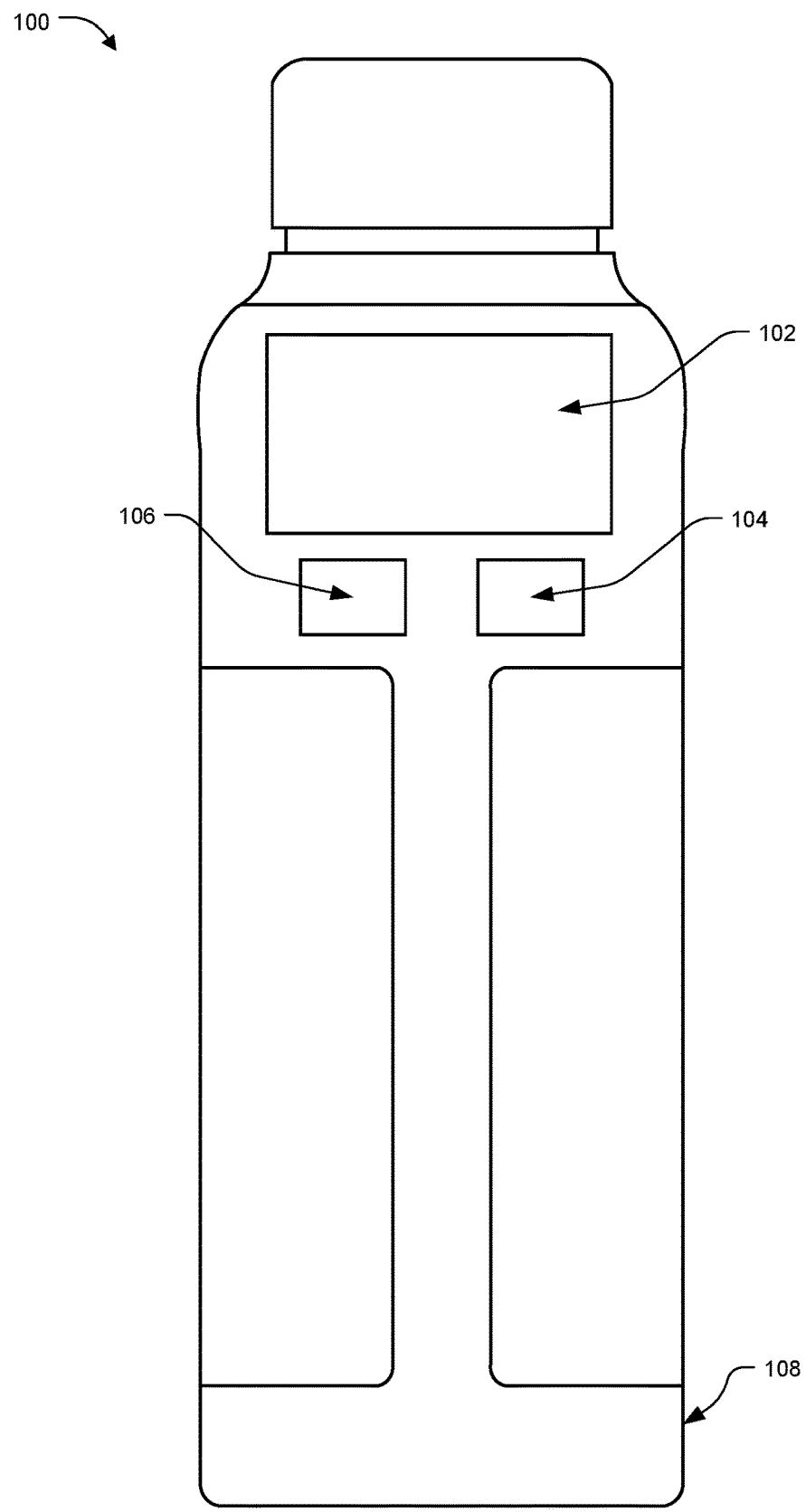
FIG. 1 illustrates an exemplary view of the water bottle incorporating screen and sensors on side cylindrical surface in accordance with an embodiment of the present disclosure.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

Various terms as used herein are shown below. To the extent a term used in a claim is not defined below, it should be given the broadest definition persons in the pertinent art have given that term as reflected in printed publications and issued patents at the time of filing.

Aspects of the present disclosure relate to a smart and intelligent water bottle that can inform its user of his hydration needs by tracking water consumed by the user. In an aspect, the bottle, while tracking water consumption by its user, can differentiate between actual consumption and intended or unintended discharge of its contents.

In an aspect, the disclosed bottle incorporates a capacitive sensor for water level measurement based on which amount of water present in the bottle and therefore amount of water consumed is calculated. In another aspect, the capacitive sensor is configured internally within a centrally located hollow space in the bottle to enable it to provide a more accurate water level reading irrespective of tilt of the bottle. Placing the sensor within a hollow space prevents it from coming in contact with water.

In an aspect, an accurate assessment of water consumption is made by providing a tilt sensor, wherein the tilt sensor can give orientation of the bottle and the reading from the capacitive sensor can be interpreted taking into account the orientation/tilt of the bottle to arrive at an accurate assessment of water quantity in the bottle. In an aspect, tilt sensing can be performed based on acceleration data received from one or more accelerometers that are configured in/with the bottle, wherein the one or more accelerometers can provide speed and duration data that can help in computing the orientation of the bottle. In an aspect, speed and duration data provided by the accelerometers and the computed tilt angle can also be used to sense if person was drinking water. There can additionally be one or more proximity sensor at mouth or spout of the bottle, and signal from the proximity sensor coupled with data from the accelerometers can be used for an accurate sensing to differentiate between actual consumption by a person and intended or unintended discharge of its contents.

In an aspect, the disclosed water bottle can besides communicating its user of his hydration needs, can also work as a safety device. In an aspect, the disclosed water bottle can incorporate a panic button for use by user in case of emergency on which the bottle can transmit a SoS and GPS co-ordinates to predefined list of friends, family or official institutions.

In an embodiment, the panic button can be configured to prevent its accidental pressing and avoid false SoS. For this purpose, the panic button can be concealed behind a hatch or a sliding part or can incorporate a 2-3 step mechanism for actuation to prevent accidental pressing.

In an aspect, the panic button can be configured to recognize a genuine pressing of the panic button and transmit a SoS and GPS co-ordinates after ascertaining genuineness of the emergency, wherein determination of the genuineness of the emergency can be based on natural increase in heart rate of the user in case of emergencies. Accordingly, pressing of the panic button can result in transmission of SoS and GPS co-ordinates to predefined list of friends, family or official institutions only if detected heart rate of the user exceeds a pre-fined heart rate.

In an embodiment, in order to facilitate easy and fast ascertaining of genuineness of emergency, the panic button can incorporate a heart rate sensor such that touching of the panic button by the user can result in sensing of heart rate. The button can be configured for a sliding motion to activate panic button functionality. Combining the heart rate sensor with the panic button and need to slide the button to meet panic button functionality can also prevent accidental pressing of the panic button.

In an embodiment, the heart rate sensor configured on the panic button can, besides helping to ascertain genuineness of the actuation of the panic button, can work as means to detect heart rate of the user such as patients, sportsmen etc.

In an embodiment, the panic button can be configured to override requirement of the sensed heart rate being more than the set threshold for sending the SoS and GPS co-ordinates. This can be implemented, for example, by providing a second sliding of the button in a direction different from the first sliding action such as in perpendicular direction.

In an embodiment, the disclosed bottle can be in Bluetooth connectivity with other computing devices such as a mobile phone/laptop/tablet PC, and transfer hydration data to an application installed in the computing device. In another embodiment, the computing device can incorporate a GSM module for wireless communication and the application can receive an indication of activation of the panic button over Bluetooth and enable transmission of the SoS and GPS co-ordinates through the GSM module of the computing device.

In an alternate embodiment, the disclosed water bottle itself can incorporate a GPS and GSM module to enable transmission of the SoS and GPS co-ordinates when the panic button is activated. A bottle that incorporate a GPS and GSM module to enable transmitting the SoS and GPS co-ordinates can meet requirement of those who may not be carrying a computing device with them such as school going children or sportsmen while engaged in sporting activity to name a few.

In an embodiment, the disclosed bottle can incorporate a touch screen for user interface. The screen can be configured at lid of the mouth of the bottle or at side cylindrical surface or at a handle among various options. The bottle can also incorporate a temperature sensor configured to sense body temperature of user. The temperature sensor can be positioned at side cylindrical surface or at handle among various options.

In an embodiment, the bottle can incorporate a processor configured to process and analyze data sensed by different sensors and signals received from buttons and compute various parameters such as tilt angle, orientation and posture of the bottle, amount of water in the bottle and accordingly water consumed by user, and thereafter issue warning/reminders to the user of his hydration need based on display in the screen or by buzzer or by warning lamps. The processor can further enable Bluetooth and/or GSM connectivity as the case may be.

In an embodiment, the GPS, processor and power storage means to power the processor and other accessories/devices can be housed at bottom of the bottle within a bottom cover or in a handle that can also incorporate panic button and temperature sensor.

Referring now to FIG. 1 wherein a water bottle 100 incorporating various disclosed features is illustrated. The bottle 100 can incorporate a touch screen 102, a temperature sensor 104, and a panic button 104 all positioned on cylindrical side face of the bottle 100. The bottle 100 can incorporate processor, GSM module GPS, batteries etc. at bottom within a bottom cover 108.

In an embodiment, the panic button 106 can be configured to prevent its accidental pressing and avoid false SoS. For this purpose, the panic button 106 can be concealed behind a hatch or a sliding part or can incorporate a 2-3 step mechanism for actuation to prevent accidental pressing.

In an embodiment, the panic button 106 can be configured to recognize a genuine pressing of the panic button and transmit a SoS and GPS co-ordinates after ascertaining genuineness of the emergency. In an embodiment, determination of the genuineness of the emergency can be based on natural increase in heart rate of the user in case of emergencies. Therefore, the panic button functionality can get activated only when sensed heart rate exceeds a pre-set threshold value. Accordingly, to facilitate easy and fast ascertaining of genuineness of the emergency the panic button 106 can incorporate a heart rate sensor such that touching of the panic button 106 by the user can result in sensing of heart rate. The button can be configured for a sliding motion to activate panic button functionality. Combining the heart rate sensor with the panic button functionality and need to slide the button to meet panic button functionality can also prevent accidental pressing of the panic button.

In an embodiment, the heart rate sensor configured on the panic button 106 can, besides helping to ascertain genuineness of the actuation of the panic button, can work as means to detect heart rate of the user such as patients, sportsmen etc.

In an embodiment, the panic button 106 can be configured to override requirement of the sensed heart rate being more than the set threshold for sending the SoS and GPS co-ordinates. This can be implemented, for example, by providing a second sliding of the button in a direction different from the first sliding action such as in perpendicular direction.

Figure 2A:
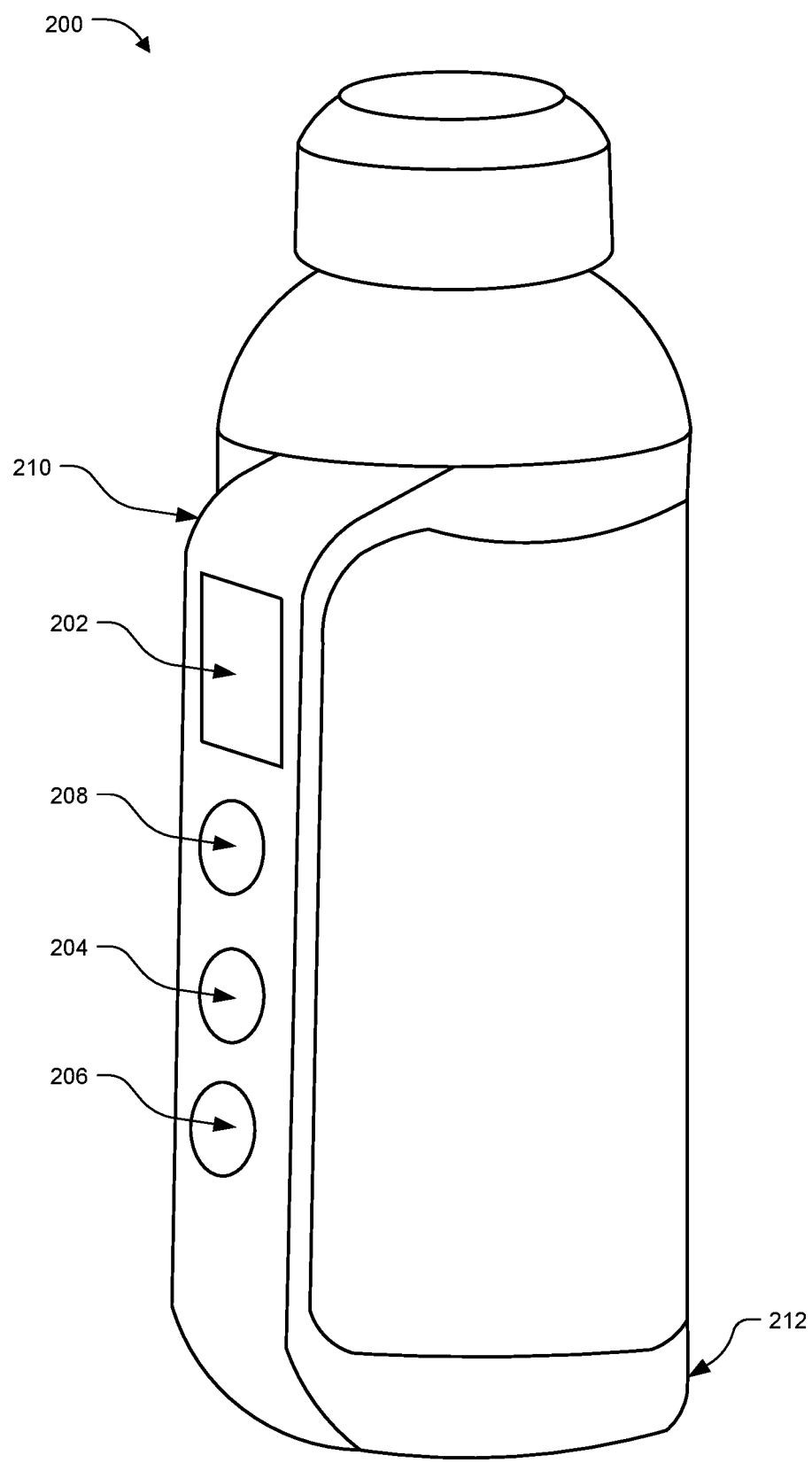
FIGS. 2A and 2B illustrate exemplary views of the water bottle incorporating screen, panic button and sensors on handle of the bottle in accordance with an embodiment of the present disclosure.
Figure 2B:
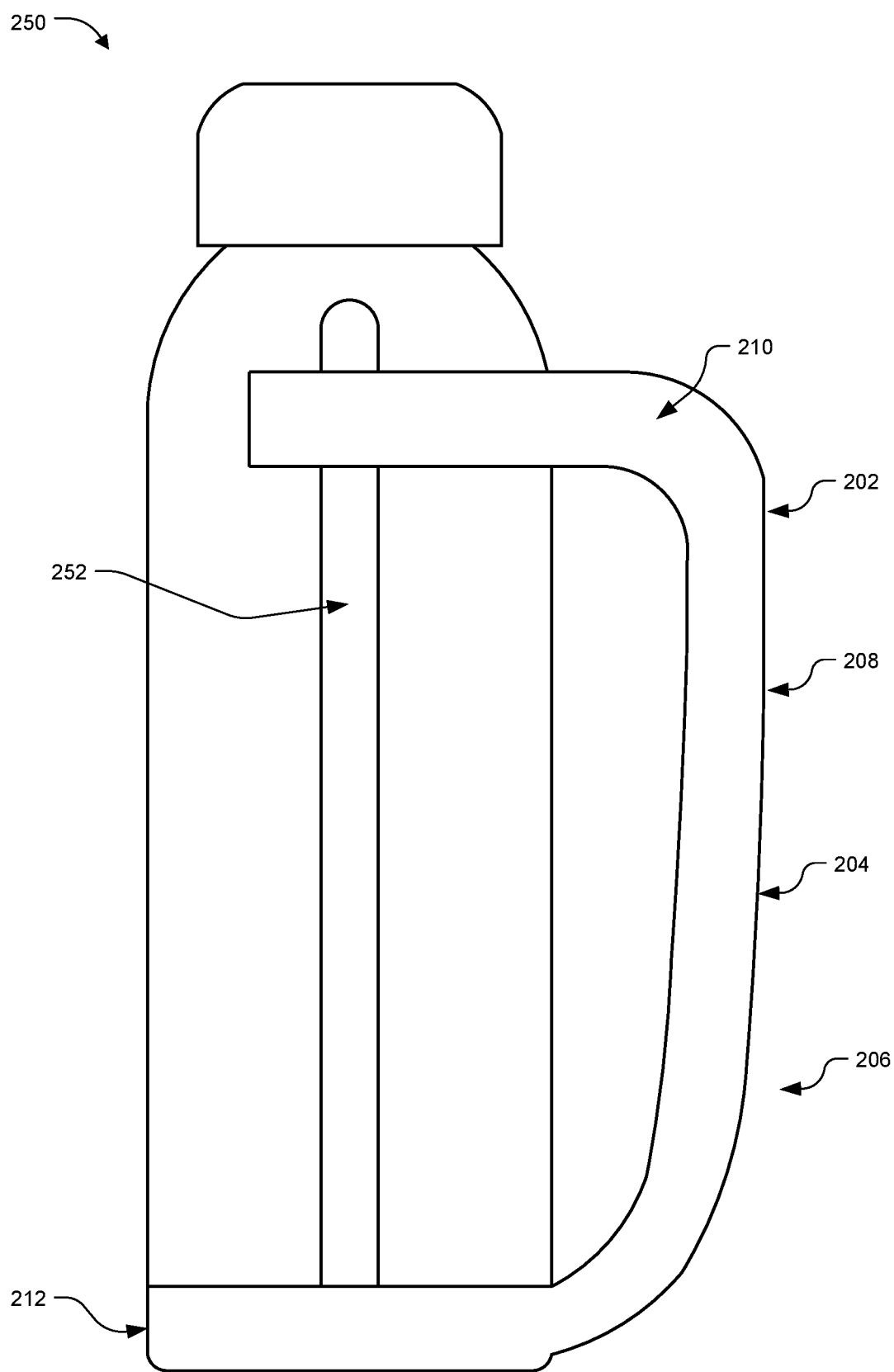

FIGS. 2A and 2B illustrate additional configurations of the disclosed water bottle, wherein bottle 200 incorporates screen 202, temperature sensor 204, panic button 206 and heart rate sensor 208 on a sensor handle 210 of the bottle. As can be seen in the bottle 200, heart rate sensor 208 can be separated from the panic button 206 and a user would be required to use two fingers for activating SoS—one for the panic button 206 and other for heart rate sensor 208. FIG. 2B shows a capacitive sensor such as a sensing tube 252 configured outside of the bottle. In another embodiment, the sensing tube 252 can be positioned inside the bottle 200 or bottle 100. As in case of bottle 100, the processor, GSM module, GPS, batteries etc. can be housed at bottom within a detachable bottom cover 212 that be an extension of the sensing handle 210.

Figure 3:
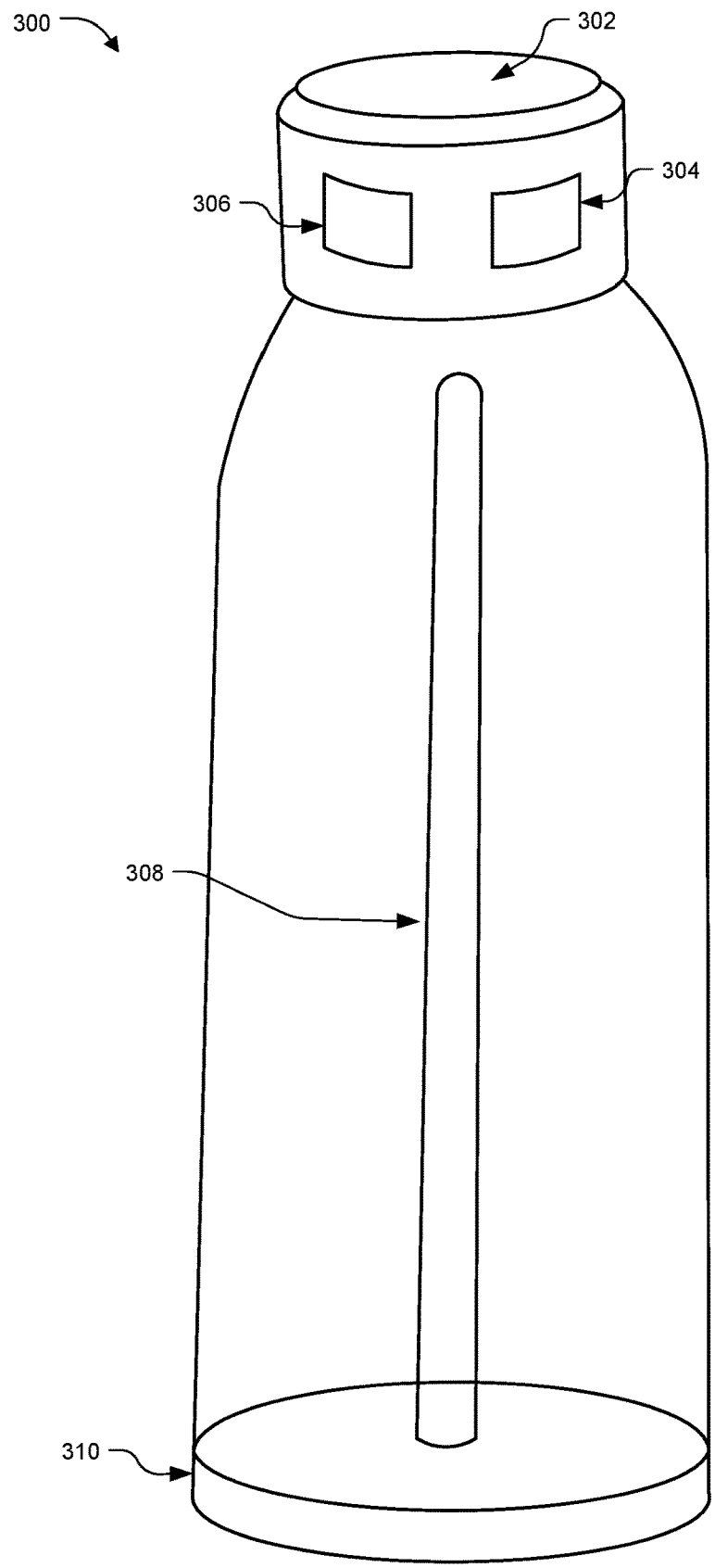
FIG. 3 illustrates an exemplary view of the water bottle incorporating screen and sensors on mouth of the bottle in accordance with an embodiment of the present disclosure.

FIG. 3 illustrates an exemplary view of another embodiment of the disclosed water bottle wherein the bottle 300 incorporates screen 302, temperature sensor 304 and panic button with a heart rate sensor 306 on mouth of the bottle 300, where the screen 302 can be configured on lid of the spout of the bottle 300. Also shown therein is capacitive sensor 308 and a detachable bottom cover 310 housing and covering the processor, GSM module, GPS, batteries etc.

Figure 4:
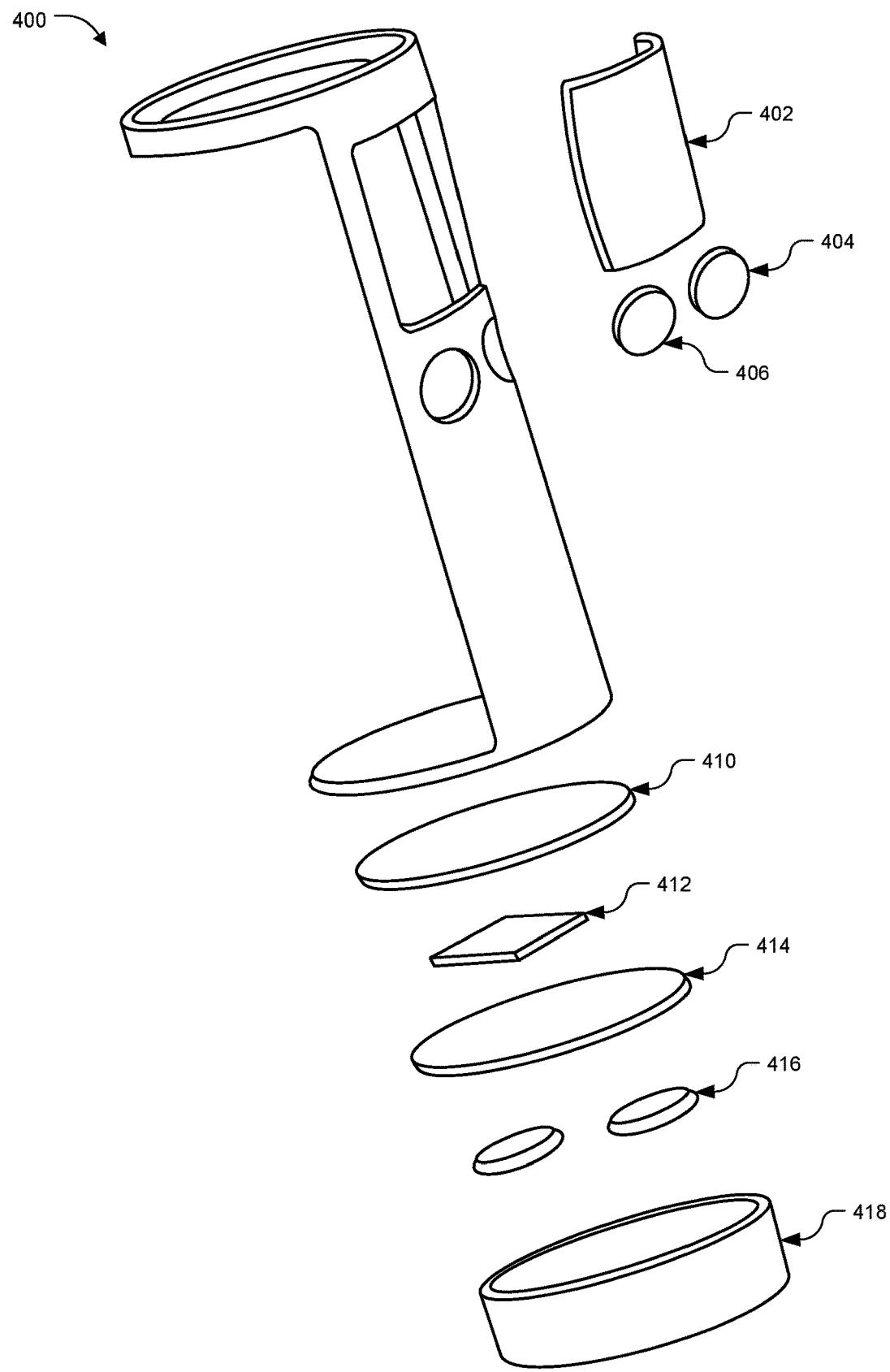
FIG. 4 illustrates an exemplary exploded view of the water bottle showing location of various parts at bottom of the bottle in accordance with an embodiment of the present disclosure.

FIG. 4 illustrates an exemplary exploded view 400 of the water bottle showing location of various parts at bottom of the bottle in accordance with an embodiment of the present disclosure. The bottom part can house one or more accelerometers on the PCB 410, a GPS 412, Processor 414 and batteries 416, and these can be covered by a bottom casing 418. Also shown are screen 402, temperature sensor 404, and heart rate sensor 406.

In an embodiment, the processor 414 can be configured to process and analyze data sensed by different sensors such as temperature sensor 404, heart rate sensor 406, capacitive sensor (not shown here) and accelerometer 410 as also signals received from buttons and compute various parameters such as tilt angle, orientation and posture of the bottle, amount of water in the bottle and accordingly water consumed by user. Thereafter, the processor 414 can issue warning/reminders to the user of his hydration need by displaying in the screen or by buzzer or by warning lamps. The processor can further enable Bluetooth and/or GSM connectivity as the case may be.

Figure 5A:
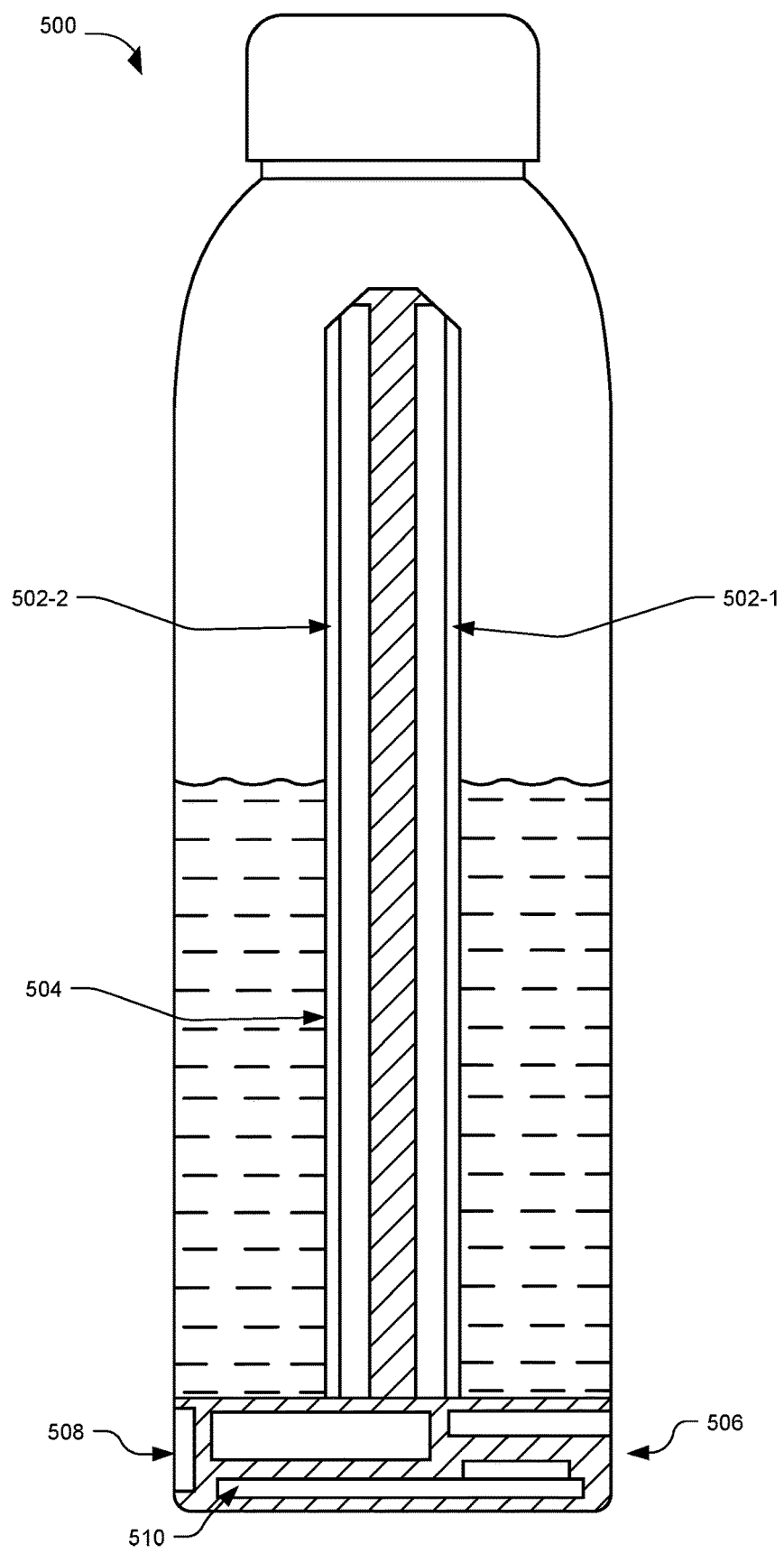
FIGS. 5A and 5E illustrate exemplary views of the water bottle in accordance with an embodiment of the present disclosure.
Figure 5B:
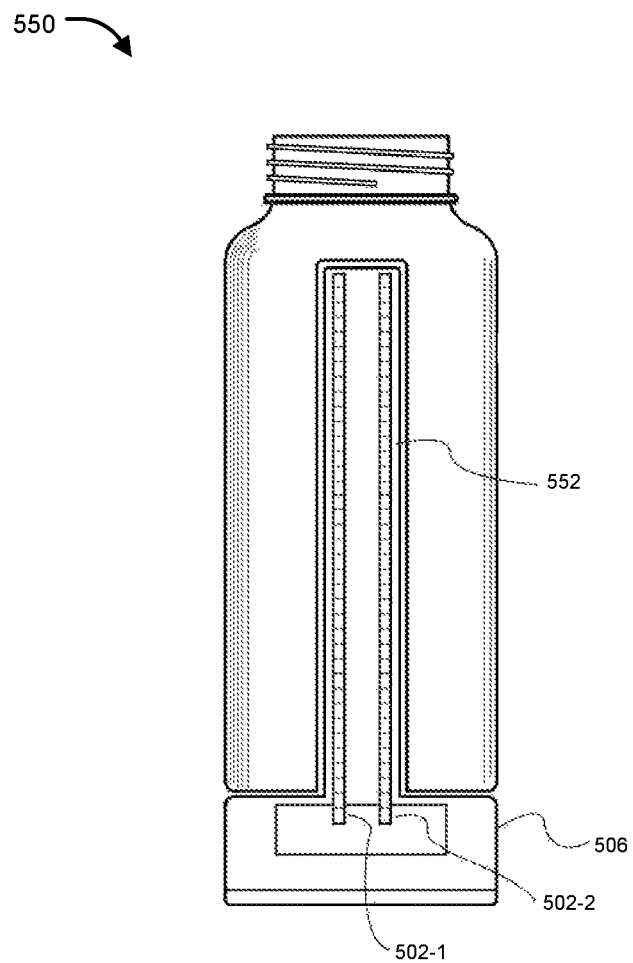
Figure 5C:
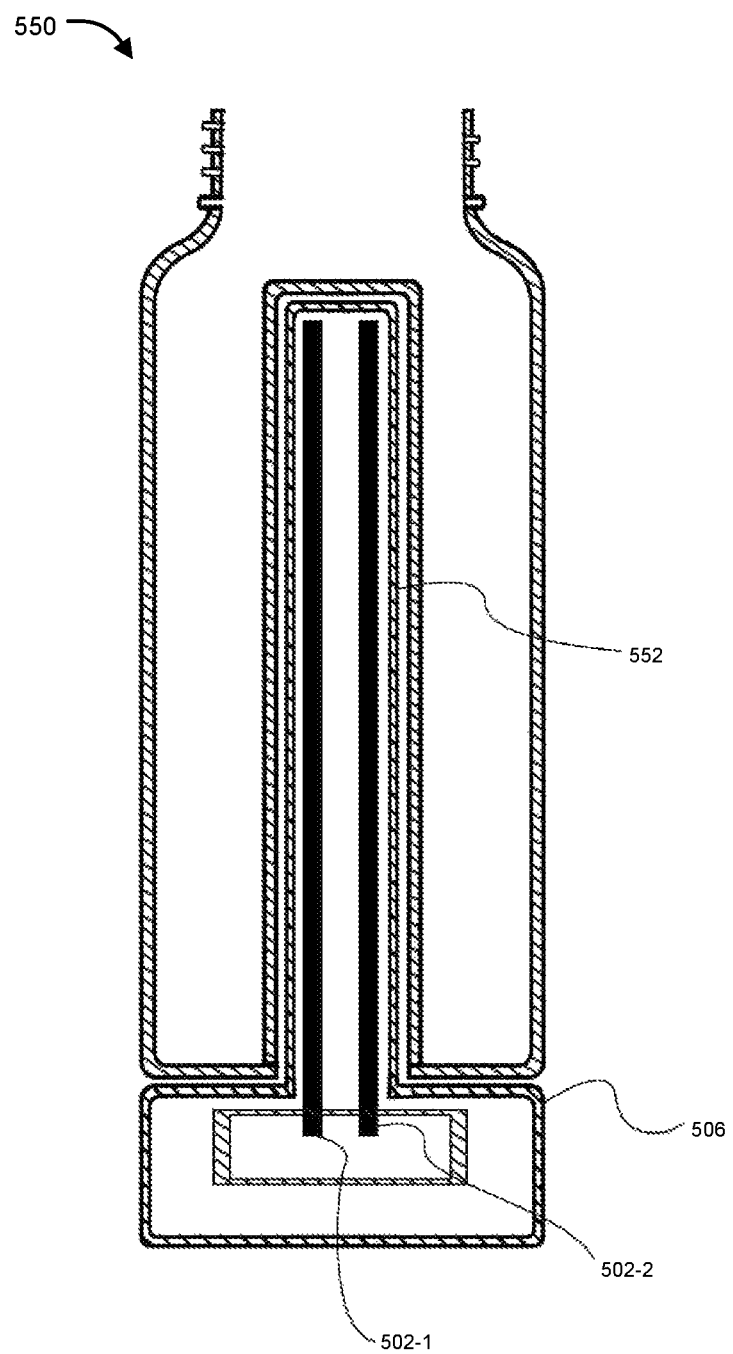
Figure 5D:
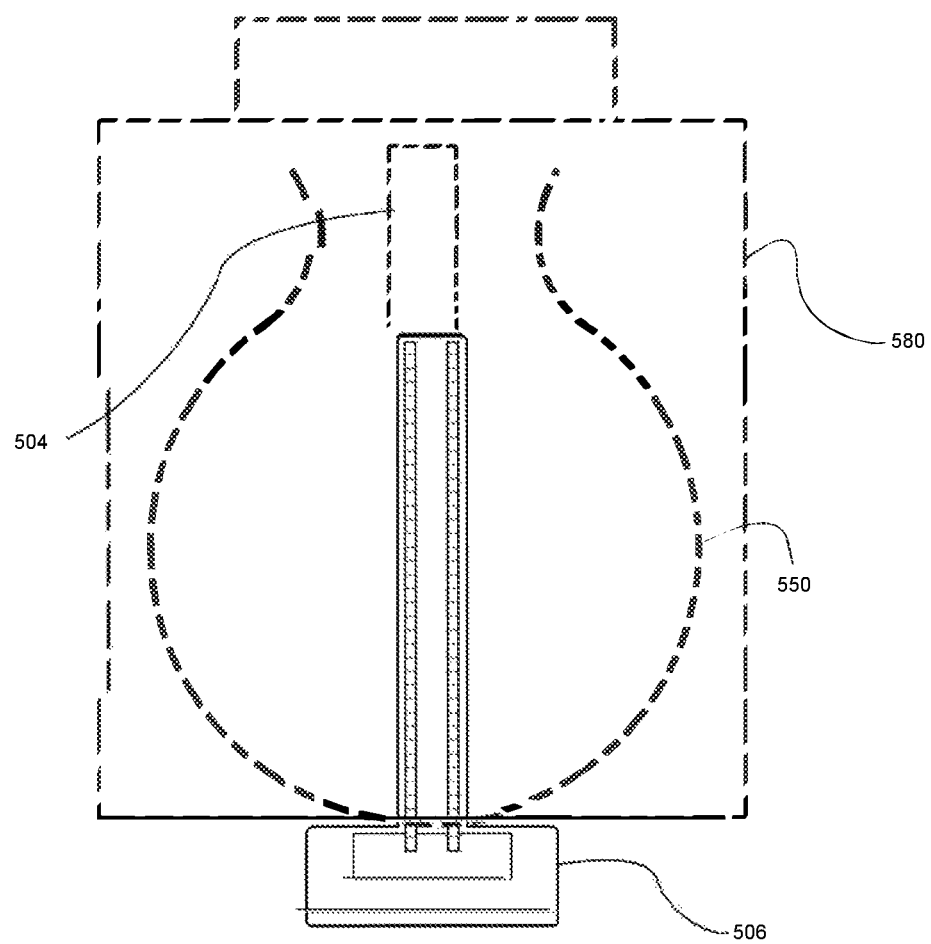
Figure 5E:
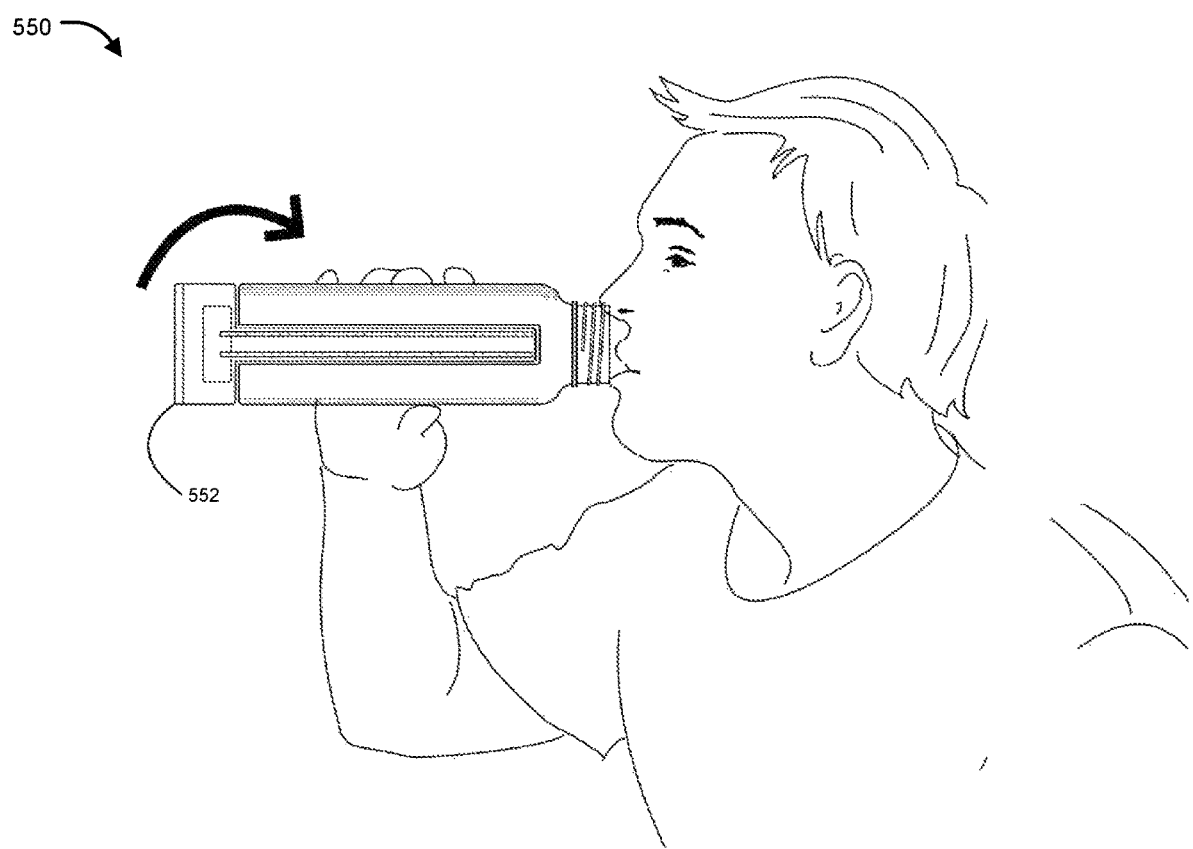

FIGS. 5A and 5E illustrate exemplary views of the water bottle in accordance with an embodiment of the present disclosure. The sectional view shows location of the capacitive sensor formed of two metal electrodes 502-1 and 502-2. The sensor is centrally located within the bottle housed within hollow space of a sensing tube 504 and thus not come in contact with water contained within the bottle 500. Locating the sensor centrally in the bottle enables it to provide a more accurate water level reading irrespective of tilt of the bottle.

The sensing tube 504 can be fixed to a bottom part 506 and accordingly can be inserted within the bottle from bottom side. The bottom part 506 can incorporate other features such as touch screen 508, heart rate sensor/panic button, temperature sensor; and also hose within it other functional parts such as controller PCB 510, accelerometers etc.

FIG. 5B shows another exemplary representation showing container/bottle 550 in accordance with an embodiment of the present disclosure. It should be appreciated that although the present disclosure has explained many embodiments of the proposed bottle as a water bottle, the proposed inventive bottle can be configured to hold any liquid such as milk, juice, or any other drink all of which are well within the scope of the present disclosure. As shown with respect to FIG. 5B, bottle 500 can include a capacitive level sensor 552 configured in a sensing tube 504, wherein the capacitive level sensor 552 can include a plurality of (such as two) capacitive electrodes 502-1 and 502-2. As explained above, the proposed bottle can be detachably coupled with the bottom part 506 having an externally connected capacitive sensor circuit. The bottom part 506 can have all the electronics required to collect data from various sensors configured on/in the bottle and process them before sending it wirelessly to a user on his/her mobile application, for instance. The data can also be stored on a cloud or any other desired database/repository as configured.

In an exemplary implementation, the bottle can be structured such that it works as a normal bottle with no measurements/water consumption readings being taken from the capacitive level sensor 552 (that is configured in the bottle) when the detachable bottom part 506 is not attached/coupled to the bottle, and once the bottom part 506 is attached to any bottle having the proposed design/capacitive level sensor 552, the sensor circuit in the bottom part 506 can couple with the capacitive electrodes 502-1 and 502-2 to read water consumption/hydration parameters factoring in other attributes such as tilt, orientation (through tilt sensor), speed, direction (through accelerators), temperature, heart rate, among other measurements. In sum, the capacitive level sensor 552 may be operative only when the bottom part 506 is attached to the bottle, which can help make the bottles modular and low cost as each bottle does not need to have the electronics embedded into it, and instead merely has to have the capacitive level sensor 552 configured in the bottles, and the bottom part 506 being modular can be fitted into bottle of any size/shape/construction that has the capacitive level sensor 552 so as to make the electronics work and readings of water hydration and others being activated.

FIG. 5C illustrates another exemplary representation of the proposed bottle design in accordance with an embodiment of the present disclosure. FIG. 5D illustrates yet another exemplary representation of the proposed bottle design in accordance with an embodiment of the present disclosure, wherein the shape/size of the bottle/vessel/container is different from that shown in FIGS. 5A to 5C. As can be seen, the capacitive electrodes 502-1 and 502-2 can extend out from the below portion of the bottle and couple with the bottom part (referred to as independent base module) 506. As also shown, the vessel can be configured in a large receptacle 580, and wherein the sensing tube 504 can be extended through incorporation of a telescoping means/mechanism. FIG. 5E shows another exemplary representation of the proposed bottle showing how a tilt sensor can be configured to recognize tilt of the bottle and can be used in conjunction with the capacitive level sensor 552 to determine the level of hydration or water consumption by the user. It can therefore be seen that the bottom portion (also referred to as base module) 506 is independent of the outer shape/size/dimension of the container/vessel/bottle as it connect with the capacitive electrodes 502 that protrude from the base of the bottle. Furthermore, the sensing tube 504 can be telescopic and therefore can be used for a container of any height.

Figure 6:
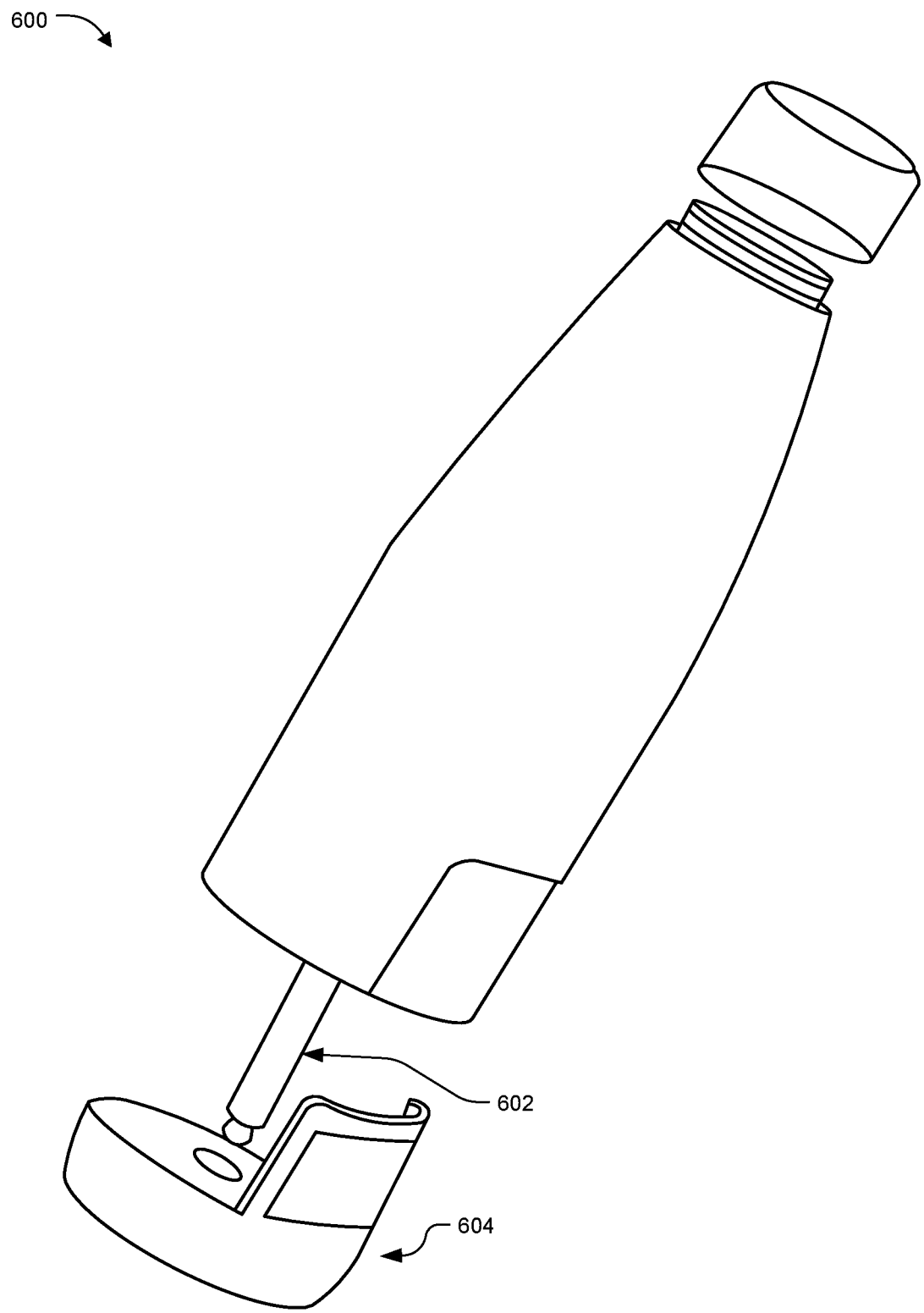
FIG. 6 illustrates an exemplary exploded view of the water bottle showing sensing tube fixed to a bottom part in accordance with an embodiment of the present disclosure.

FIG. 6 illustrates an exemplary exploded view of the water bottle 600 in accordance with an embodiment of the present disclosure. As shown therein, the sensing tube 602 can be fixed to the bottom part 604 and inserted from bottom of the bottle.

Figure 7A:
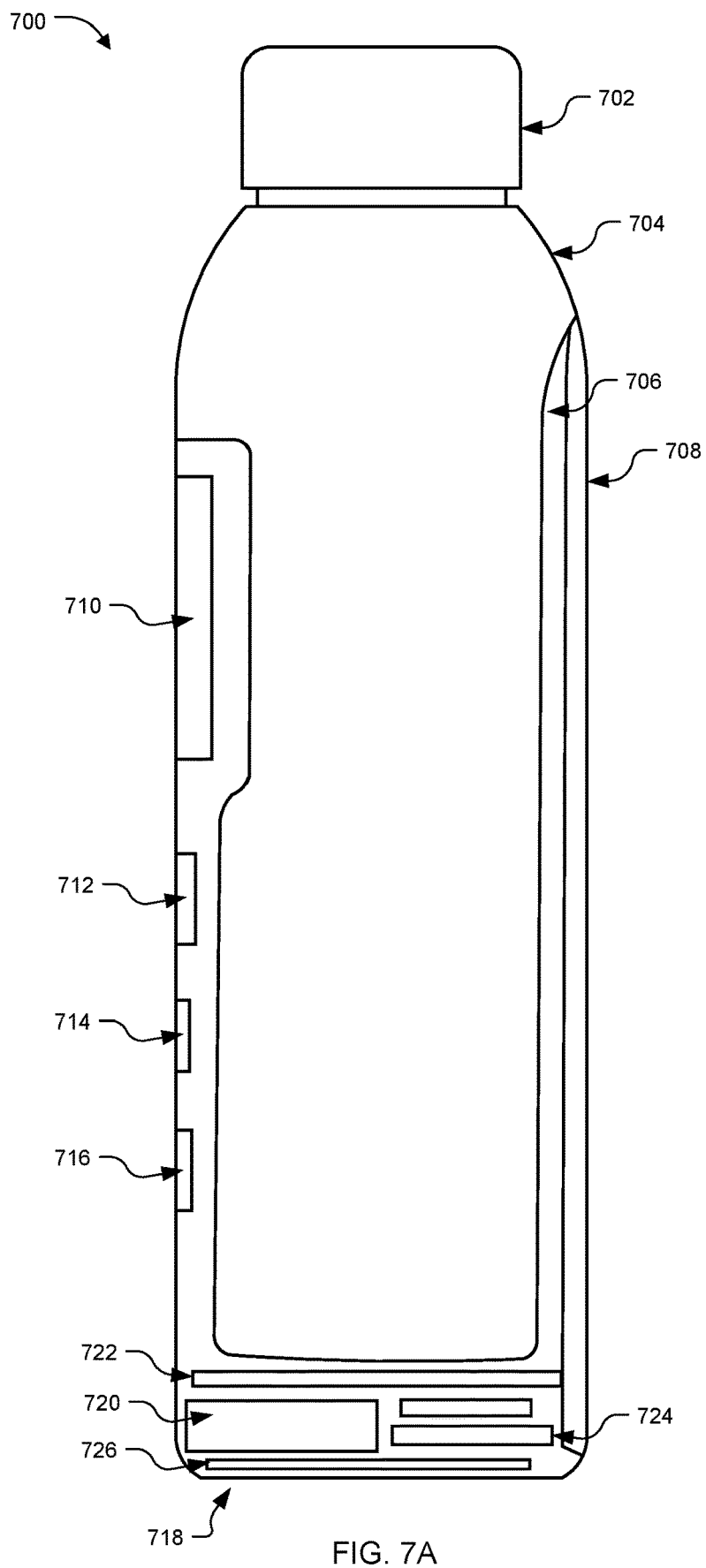
FIG. 7A illustrates another exemplary representation of the proposed bottle in accordance with an embodiment of the present disclosure.

FIG. 7A illustrates another exemplary representation of the proposed bottle 700 in accordance with an embodiment of the present disclosure. As shown, the bottle 700 includes a spout 702 and a container 704, wherein the container body 704 includes a capacitive level sensor 706 on one edge of the container 704, said sensor 706 comprising one or more electrodes 708. In an aspect, as mentioned above, said sensor 706 can be detachably configured in the container 704 by means of a detachable base/bottom 718, and can be taken out from the bottom/base of the container 704 as and when desired. As can also be seen, the container 704 can include any or a combination of a touch screen 710, a heart rate sensor 712, a SOS button 714, and a temperature sensor 716. In an aspect, the detachable base/bottom 718 can include a battery such as a lithium rechargeable battery 720, a controller PCB 722 that enables/controls operation of the sensor 706. It would be appreciated these are only exemplary implementations and any other configuration that enables aspects of the present invention is completely within the scope of the present invention. For instance, the temperature sensor and/or heart rate sensor can always be configured in the detachable base/bottom 718 or in the spout 702. In another aspect, the base/bottom 718 can further include a charging PCB 724 and/or an inductive charging plate 726. As can also be seen, the sensor 706 need not be configured centrally in the bottle and can also be configured along one or both edges of the container.

Figure 7B:
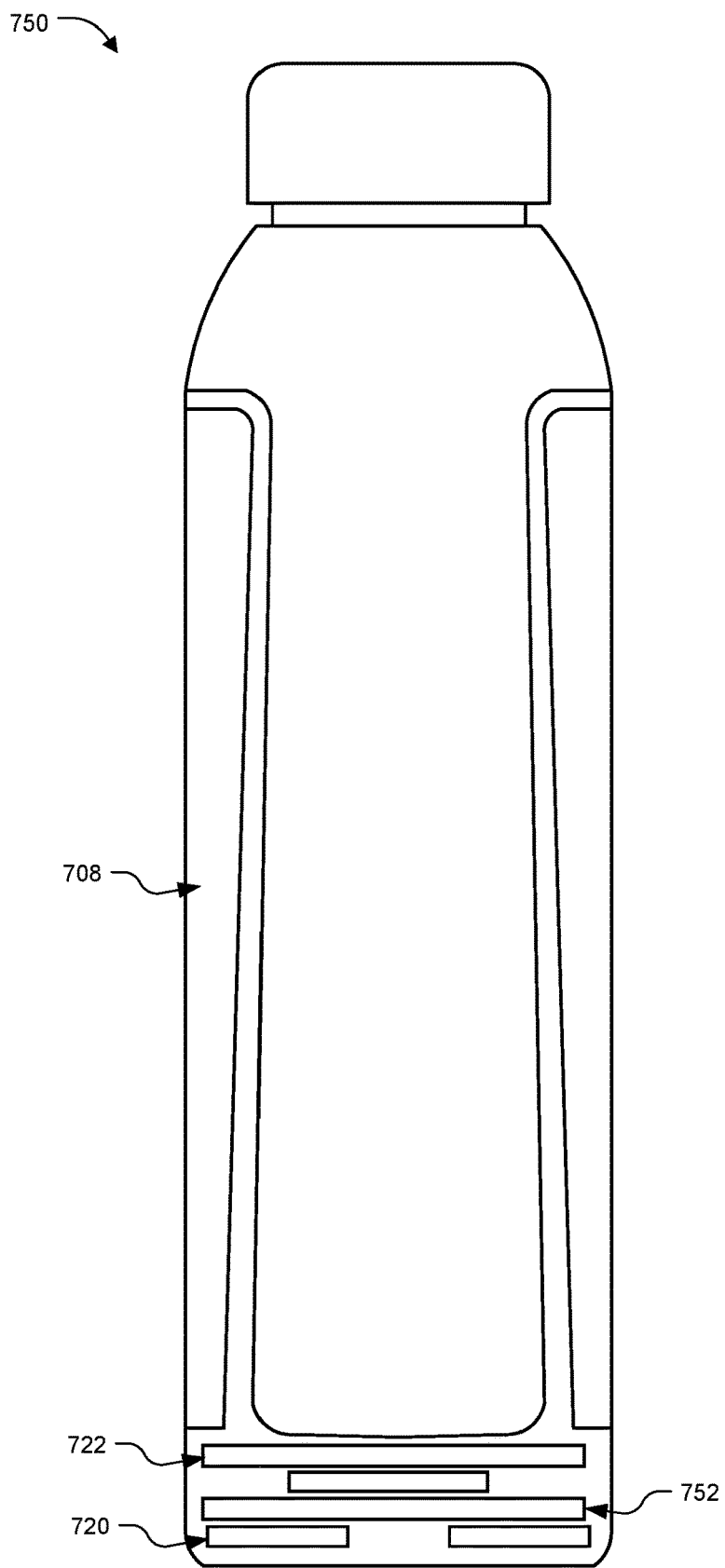
FIG. 7B illustrates another exemplary representation of the proposed bottle in accordance with an embodiment of the present disclosure.

FIG. 7B illustrates another exemplary representation 750 of the proposed bottle in accordance with an embodiment of the present disclosure, wherein the bottle comprises capacitive electrodes like 708, controller PCB such as 722, battery such as 720, and a GPS 752 to help determine and transmit location coordinates of the user of the bottle.

Figure 8A:
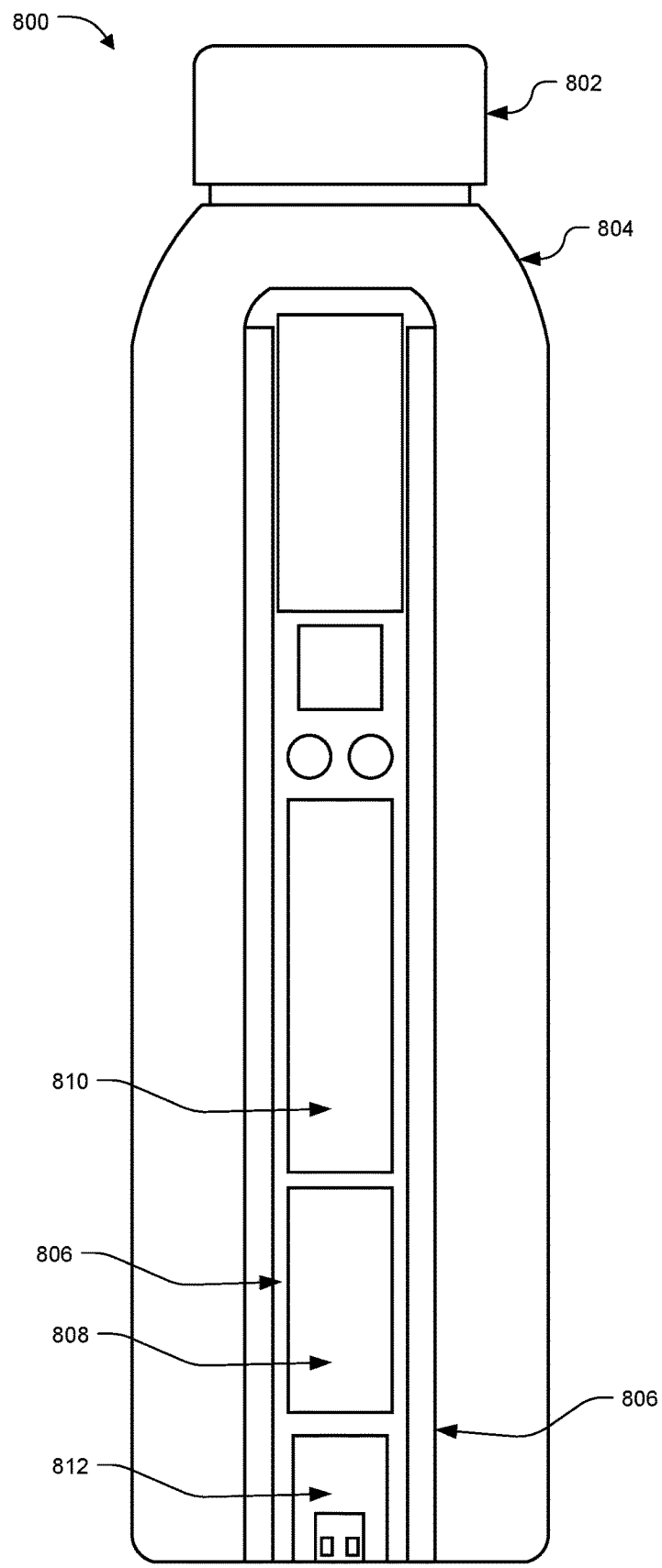
FIG. 8A illustrates another exemplary representation of the proposed bottle design configured with an independent sensing strip in accordance with an embodiment of the present disclosure.

FIG. 8A illustrates another exemplary representation of the proposed bottle design configured with an independent sensing strip 850 in accordance with an embodiment of the present disclosure. As shown, the bottle 800 includes a spout 802 and a container 804, wherein the container body 804 includes a capacitive level sensor configured along the center of the container 804 and supported, for instance, by means of a detachable bottom/base, said sensor comprising one or more electrodes 806. In an aspect, the container 804 can further include or be operatively coupled with a battery 808 to enable operation of the sensor/electrodes, a controller PCB 810 to control functioning of the sensor/electrodes, and a charging PCB 812 that enables/controls operation of the sensor.

Figure 8B:
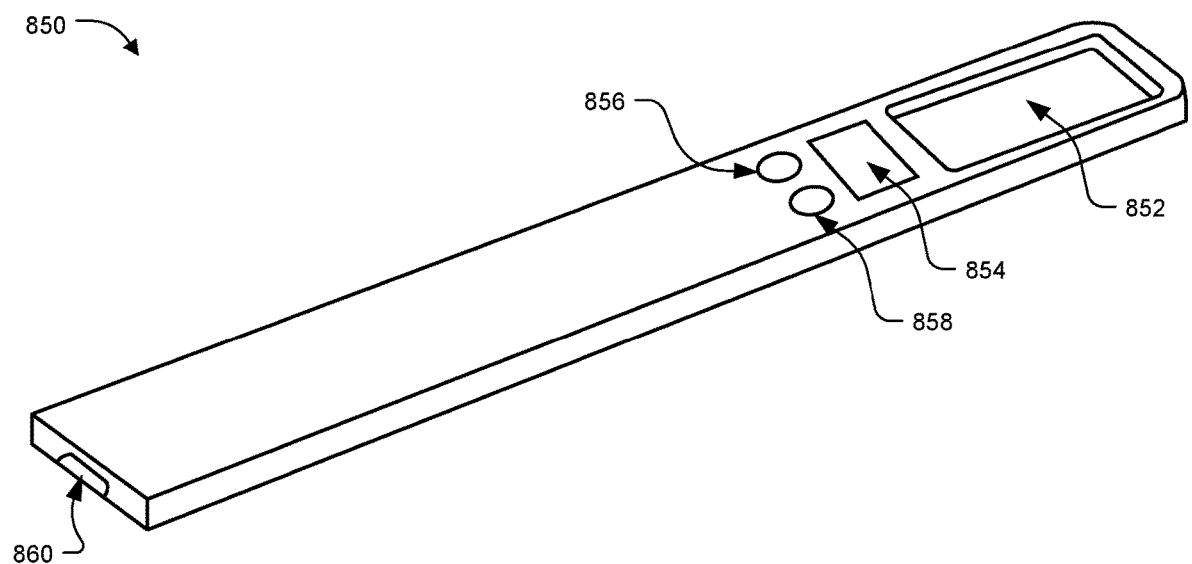
FIG. 8B illustrates an exemplary representation of the independent sensing strip 850 having a charging slot 860 that can be used to charge the strip, which being independent, can be used on any bottle.

In an aspect, the strip 850 can be configured externally on the bottle 800 and can include any or a combination of a touch screen 852, a heart rate sensor 854, a SOS button 856, and a temperature sensor 858. Therefore, such a strip 850 can be used on any bottle to instantly enable the measurement and display of parameters of the bottle. FIG. 8B illustrates an exemplary representation 850 of the independent sensing strip 850 having a charging slot 860 that can be used to charge the strip 850, which being independent, can be used on any bottle.

Figure 9:
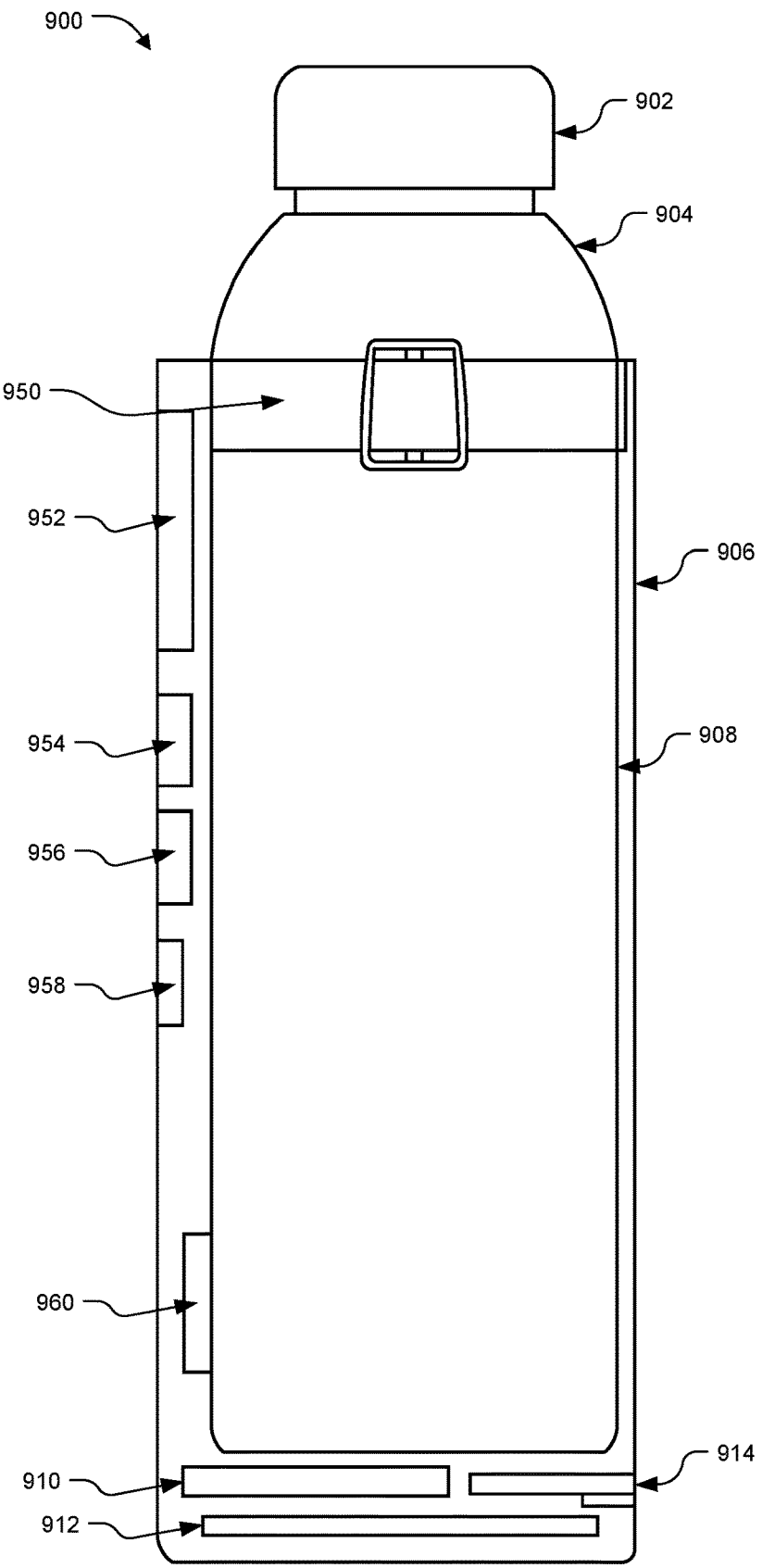
FIG. 9 illustrates yet another exemplary representation of the proposed bottle design in accordance with an embodiment of the present disclosure.

FIG. 9 illustrates yet another exemplary representation of the proposed bottle design in accordance with an embodiment of the present disclosure, wherein the bottle 900 is operatively coupled with an adjustable strap 950 that comprises the touch screen 952, heart rate sensor 954, temperature sensor 956, SOS button 958, and GPS 960, whereas the container 904 of the bottle 900 (also having spout 902) includes the capacitive sensor 906/electrodes 908, battery 910, controller PCB 912, and a charging PCB 914.

Figure 10A:
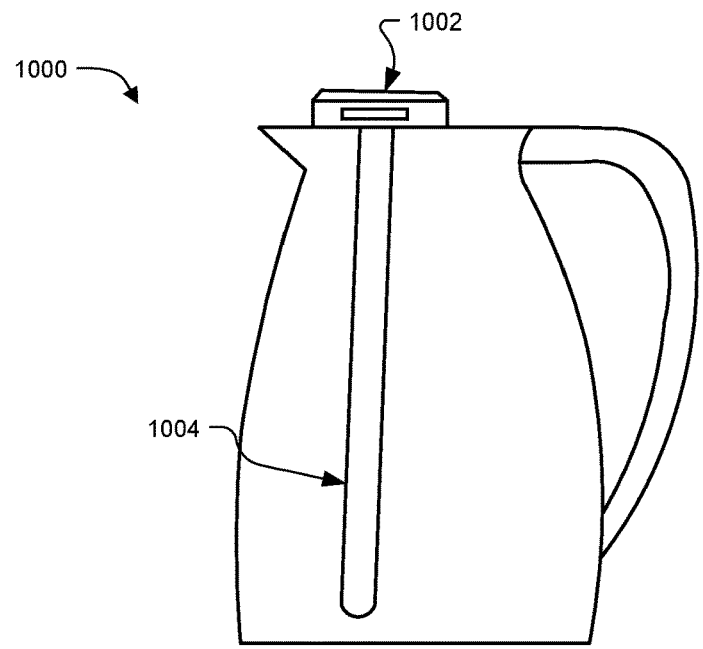
FIG. 10A illustrates implementation of the proposed capacitive sensor in jug or bottle of another form factor.
Figure 10B:
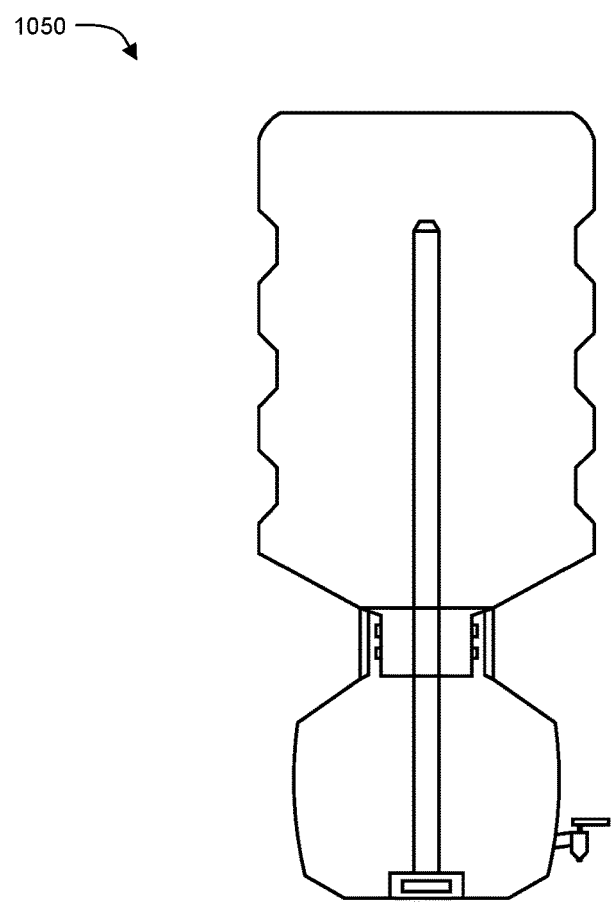
FIG. 10B shows another container form factor where the detachable assembly having the capacitive sensor/electrodes can be configured in the water filter/water outlet/water cooler over which replacement water container can be fitted.

FIG. 10A illustrates implementation of the proposed capacitive sensor in jug or bottle 1000 of another form factor, wherein instead of a detachable bottom, a detachable assembly 1002 having the capacitive sensor 1004 can be incorporated that can be configured from the top of the jug 1000. As the assembly 1002 is still detachable, it can be put in any other container of any form factor of whose the water level is to be measured/assessed. FIG. 10B shows another container form factor where the detachable assembly having the capacitive sensor/electrodes can be configured in the water filter/water outlet/water cooler over which replacement water container can be fitted.

In yet another aspect, the proposed bottle can form part of a computing system/architecture, wherein a user can be allowed to undergo registration with the system, based on which his/her water/liquid/fluid consumption patterns can be transmitted to a central server/cloud and logged accordingly. Using such an architecture, even though user may drink water from multiple bottles (one at home, one at office, and another one at gym), each bottle, by means of its GSM/GPS and communication means can be associated uniquely with the user and transmit his/her water consumption details (such as volume and time of consumption) to the server/cloud. In another exemplary implementation, enabling user registration through fingerprint (or any other biometric means) authentication, the proposed can be configured to persist the hydration calculation for the user even if the user has the need to use multiple bottles in parallel or sequentially where replacements and new purchases happen. A biometric authentication means can therefore be configured on/in the bottle, which can authenticate as well as uniquely identify the user to then transmit his/her water consumption details to the server/cloud through a secured connection.

In an aspect therefore, the proposed bottle can be operatively coupled with a computing device/server/cloud, and configured to transmit one or more liquid consumption parameters of a user to the computing device, wherein the bottle can include a biometric authentication means configured to uniquely identify the user in a manner such that if the user consumes the liquid from a second bottle, said second bottle also uniquely identifies the user and liquid consumption parameters from the bottle and the second bottle for the user are stored together at the computing device. As mentioned above, the one or more liquid consumption parameters are selected from any or a combination of volume of liquid consumption, timing of liquid consumption, and volume of water consumption at each instance of consumption.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

Advantages of the Invention

The present disclosure provides a smart and intelligent water bottle that can inform its user if his hydration needs are met or not.

The present disclosure provides a water bottle that besides overcoming drawbacks of the known smart bottles incorporates other desired functionalities.

The present disclosure provides a water bottle with a capacitive sensor placed in a centrally located hollow space within the bottle to measure water level so that the sensor makes a more accurate measure of the water level and also does not come in contact with water.

The present disclosure provides a water bottle that makes an accurate assessment of water consumption by using tilt of the bottle for accuracy of water level measurement.

The present disclosure provides a water bottle that can differentiate between actual consumption and intended or unintended discharge of its contents.

The present disclosure provides a user safety device in form of a water bottle by providing a panic button for use by its user in case of an emergency The present disclosure provides a water bottle that can send SOS and GPS co-ordinates to predefined list of friends, family or official institutions.

The present disclosure provides a water bottle that can recognize a genuine pressing of the panic button.

The present disclosure provides a water bottle that can recognize a genuine pressing of the panic button based on heart rate of user.

We claim:

1. A bottle for holding a liquid, said bottle comprising:
   a sensing tube configured to hold at least one capacitive sensor formed of one or more metal electrodes, wherein the at least one capacitive sensor is configured centrally in the bottle and is housed in a hollow space of the sensing tube, and wherein the at least one capacitive sensor is configured to provide an accurate water level reading, and wherein the one or more metal electrodes protrude out from the base of the bottle; and
   a bottom part that is detachably coupled with the base of the bottle and comprises a processor such that when the bottom part is attached to the bottle, the at least one capacitive sensor is activated and water level reading and other hydration parameters are computed by the processor, and when the bottom part is not attached with the bottle, the at least one capacitive sensor is not activated.

2. The bottle of claim 1, wherein the bottom part further comprises any or a combination of a touch screen, a heart rate sensor, a panic button, a temperature sensor, and one or more accelerometers.

3. The bottle of claim 1, wherein the bottom part is operatively coupled with the sensing tube such that the sensing tube forms part of the bottle only when the bottom part is attached to the base of the bottle.

4. The bottle of claim 1, wherein the bottle comprises a tilt sensor configured to sense any or a combination of tilt angle, orientation, and posture of the bottle, and wherein outputs from the tilt sensor and the at least one capacitive sensor are processed by the processor to issue reminder to user of his/her hydration need.

5. The bottle of claim 1, wherein the bottle is operatively coupled with a computing device and configured to transmit one or more liquid consumption parameters of a user to the computing device.

6. The bottle of claim 5, wherein the bottle comprises a biometric authentication means configured to uniquely identify the user in a manner such that if the user consumes the liquid from a second bottle, said second bottle also uniquely identifies the user and liquid consumption parameters from the bottle and the second bottle for the user are stored together at the computing device.

7. The bottle of claim 5, wherein the one or more liquid consumption parameters are selected from any or a combination of volume of liquid consumption, timing of liquid consumption, and volume of water consumption at each instance of consumption.

8. A bottle for holding a liquid, said bottle comprising:
   a panic button configured on outer surface of the bottle and operatively coupled with a communication means;
   a location determination means configured to output location of a user of the bottle; and
   a heart rate sensor configured to output heart rate of the user of the bottle when said panic button is pressed by the user such that an emergency signal is transmitted based on the heart rate of the user, and wherein said emergency signal is transmitted along with the location of the user.

9. The bottle of claim 8, wherein the location determination means is a GPS device.

10. The bottle of claim 8, said bottle further comprising a sensing tube configured to hold at least one capacitive sensor formed of one or more metal electrodes, wherein the sensor is configured centrally in the bottle and is housed in a hollow space of the sensing tube, and wherein the at least one capacitive sensor is configured to provide an accurate water level reading.

11. The bottle of claim 10, wherein the bottle is detachably coupled with a bottom part in a manner such that when the bottom part is attached to the bottle, the at least one capacitive sensor is activated and water level reading and other hydration parameters are computed, and when the bottom part is not attached with the bottle, the at least one capacitive sensor is not activated.

12. The bottle of claim 10, wherein the bottle or the bottom part comprises a touch screen.

13. The bottle of claim 10, wherein the bottle or the bottom part comprises any or a combination of a temperature sensor, one or more accelerometers, and a GSM module.

14. The bottle of claim 10, wherein the bottom part comprises a controller PCB.

15. The bottle of claim 8, wherein the bottle comprises any or a combination of a touch screen, a temperature sensor, a processor, a GSM module, a battery, and a GPS.

16. The bottle of claim 8, wherein the panic button is concealed behind a hatch or a sliding part of the bottle so as to prevent accidental pressing.

17. The bottle of claim 8, wherein the emergency signal is transmitted when the heart rate of the user is greater than a defined threshold.

18. The bottle of claim 8, wherein the emergency signal is bypassed by another physical action taken on a button configured on the bottle.

19. The bottle of claim 8, wherein the communication means is selected from any or a combination of a wireless communication means, Bluetooth, Wi-Fi, RFID, Zigbee.

20. A bottle for holding a liquid, said bottle comprising: at least one capacitive sensor formed of one or more metal electrodes, wherein the at least one capacitive sensor is configured in the bottle, and wherein the at least one capacitive sensor is configured to provide an accurate water level reading, and wherein the one or more metal electrodes protrude out from the base of the bottle; and a bottom part that is detachably coupled with the bottle and comprises a processor such that when the bottom part is attached to the bottle, the at least one capacitive sensor is activated and water level reading and other hydration parameters are computed by the processor, and when the bottom part is not attached with the bottle, the at least one capacitive sensor is not activated.

* * * * *